(12) United States Patent
Garel (10) Patent No.: US 9,334,216 B2
(45) Date of Patent: May 10, 2016

(54) METHOD FOR PRODUCING ALKOXYPHENOL AND ALKOXY-HYDROXYBENZALDEHYDE

(71) Applicant: RHODIA OPERATIONS, Paris (FR)

(72) Inventor: Laurent Garel, Lyons (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/417,015

(22) PCT Filed: Jul. 12, 2013

(86) PCT No.: PCT/EP2013/064861
§ 371 (c)(1),
(2) Date: Jan. 23, 2015

(87) PCT Pub. No.: WO2014/016146
PCT Pub. Date: Jan. 30, 2014

(65) Prior Publication Data
US 2015/0183702 A1 Jul. 2, 2015

(30) Foreign Application Priority Data
Jul. 26, 2012 (FR) ...................................... 12 57275

(51) Int. Cl.
| C07C 45/38 | (2006.01) |
| C07C 51/353 | (2006.01) |
| C07C 41/06 | (2006.01) |
| C07C 41/16 | (2006.01) |
| C07C 51/367 | (2006.01) |
| C07C 45/54 | (2006.01) |

(52) U.S. Cl.
CPC .................. *C07C 45/38* (2013.01); *C07C 41/06* (2013.01); *C07C 41/16* (2013.01); *C07C 45/54* (2013.01); *C07C 51/353* (2013.01); *C07C 51/367* (2013.01)

(58) Field of Classification Search
CPC ...... C07C 45/32; C07C 45/455; C07C 37/055
USPC .......................................................... 568/432
See application file for complete search history.

(56) References Cited

U.S. PATENT DOCUMENTS

| 3,274,260 A | 9/1966 | Levy et al. |
| 3,374,276 A | 3/1968 | Swidinsky |
| 4,165,341 A | 8/1979 | Umemura et al. |
| 4,465,868 A | 8/1984 | Maekawa et al. |
| 5,430,183 A | 7/1995 | Nobel |
| 5,948,909 A | 9/1999 | Buizer et al. |
| 6,753,441 B1 | 6/2004 | Jouve et al. |
| 2011/0009664 A1 | 1/2011 | Heinisch et al. |
| 2011/0230674 A1 | 9/2011 | Desouhant-Massacret |
| 2011/0306802 A1 | 12/2011 | Maliverney et al. |
| 2012/0103786 A1 | 5/2012 | Gayet et al. |
| 2012/0264982 A1 | 10/2012 | Desouhant-Massacret |

FOREIGN PATENT DOCUMENTS

| CN | 102010310 A | 4/2011 |
| EP | 0578550 A1 | 1/1994 |
| FR | 2379501 A1 | 12/2011 |
| WO | WO 99065853 | 12/1999 |
| WO | WO 2008148760 A1 | 12/2008 |
| WO | WO 2009077383 A1 | 6/2009 |
| WO | WO 2009141280 A1 | 11/2009 |
| WO | WO 2010007161 A1 | 1/2010 |
| WO | WO 2011039331 A1 | 4/2011 |
| WO | WO2014/016145 A1 | 1/2014 |

OTHER PUBLICATIONS

U.S. Appl. No. 14/417,010, filed Jan. 23, 2015, Garel.
Bjorsvik et al. —High Selectivity in the Oxidation of Mandelic Acid Derivatives and in O-Methylation of Photocatechualdehyde: New Processes for Synthesis of Vanillin, iso-Vanillin, and Heliotropin, Organic Process Research & Development (2000), vol. 4, No. 6, 534-543 (10 pages).
Markey et al.—General Methods for the Synthesis of Mythyl Isotope Labelled Catecholamine Metabolites; Preparation of 4-hydroxy-3-methoxy-d3-(mandefic acid, phenyiacetic acid, and phenylethylene glycol), Journal of Labelled Compounds and Radiopharmaceuticals (1980) vol. 17, No. 1, 103-114 (12 pages).
English translation of Office Action issued in corresponding Chinese Application No. 201380011980.9, mailed Jun. 23, 2015 (13 pages).

*Primary Examiner* — Sikarl Witherspoon
(74) *Attorney, Agent, or Firm* — Osha Liang LLP (57) ABSTRACT

The invention relates to a method for producing alkoxyphenol from hydroxyphenol, comprising an O-alkylation reaction of at least one hydroxyphenol into at least one alkoxyphenol, said reaction being carried out using an O-alkylating agent, an aqueous solvent containing a Brönsted base, and an organic solvent, with a base/O-alkylating agent ratio of between 0.5 and 1.5 in moles of base per mole of O-alkylating agent, an O-alkylating agent/hydroxyphenol ratio of between 0.5 and 2 moles of O-alkylating agent per mole of hydroxyphenol, and an organic solvent/hydroxyphenol ratio of less than 280 mL, preferably between 10 and 250 mL and more preferably still between 50 and 150 mL of organic solvent per mole of hydroxyphenol. The invention also relates to a method for producing at least one alkoxy-hydroxybenzaldehyde from at least one hydroxyphenol compound.

15 Claims, 2 Drawing Sheets

METHOD FOR PRODUCING ALKOXYPHENOL AND ALKOXY-HYDROXYBENZALDEHYDE

This application is a U.S. national stage entry under 35 U.S.C. §371 of International Application No. PCT/EP2013/064861, filed Jul. 12, 2013, which claims priority to French Application No. 1257275 filed on Jul. 26, 2012. The entire content of each of these applications is hereby incorporated herein.

TECHNICAL FIELD OF THE INVENTION

The present invention relates to a process for producing at least one alkoxyphenol compound from at least one hydroxyphenol.

The present invention also relates to a process for producing at least one alkoxyhydroxybenzaldehyde compound from at least one hydroxyphenol compound. The present invention relates more specifically to a process for synthesizing vanillin (VA or 4-hydroxy-3-methoxybenzaldehyde) and/or ethylvanillin (EVA or 3-ethoxy-4-hydroxybenzaldehyde). The present invention relates in particular to a process for producing vanillin and/or ethylvanillin from a precursor of guaiacol and/or of guaethol, and in particular from pyrocatechol.

PRIOR ART

Alkoxyhydroxybenzaldehydes are very important products used first as flavorings and fragrances and then subsequently as intermediate products in numerous fields, for instance agrochemistry, pharmacy, the cosmetics industry and other industries.

In particular, vanillin and ethylvanillin are products that are essentially intended for foods. It is therefore important to offer the market products which are of high chemical purity and of good taste quality while at the same time ensuring a marketing cost that is as low as possible.

Thus, the process for synthesizing said products requires an improvement in the chemical reactions carried out and the performing of efficient separation and purification operations.

Various processes have been proposed for the synthesis of aromatic aldehydes. The most significant processes are based on the functionalization of a starting phenolic compound, for example phenol, catechol, catechol derivative, guaiacol (or 2-methoxyphenol) or guaethol (or 2-ethoxyphenol). In this type of process, the phenolic compound is generally used in a salified form, for example, in the form of a sodium salt: a formyl group is added in the para position with respect to the hydroxyl group present on the benzene ring, according to various methods.

To produce guaiacol, some processes consist in choosing ortho-nitrochlorobenzene (ONCB) as starting material.

These processes have many drawbacks compared with the process starting from pyrocatechol: handling of CMR (carcinogenic, mutagenic and toxic to reproduction) toxic compounds, such as o-anisidine; numerous steps; exothermic and dangerous reactions, such as nitration or hydrolysis of a diazonium salt; generation of a large amount of effluents; formation of impurities, such as 5-chloroguaiacol, which are in vanillin in the form of 6-chlorovanillin, etc.

Moreover, there is a completely different route for obtaining vanillin, which consists in reacting guaiacol and glyoxylic acid in a basic medium, resulting in 4-hydroxy-3-methoxymandelic acid, and then in oxidizing the condensate obtained.

Synthesizing guaiacol or guaethol from pyrocatechol is much more direct.

Processes for synthesizing para-methoxyphenol (PMP, also known as MEHQ for hydroquinone monomethyl ether) from hydroquinone also exist. PMP is used, for example, in industry as a polymerization inhibitor or as an antioxidant.

AIMS OF THE INVENTION

These routes of access require improvement, and in particular the route of access starting from pyrocatechol and/or from hydroquinone. An aim of the present invention is to manufacture the alkoxyphenol compound industrially with a good yield, a low production of impurities and/or efficient removal thereof, and a high hydroxyphenol conversion, while at the same time limiting the costs of such a production. An aim of the invention is in particular to produce this alkoxyphenol compound on the basis of an O-alkylation reaction using an O-alkylating agent. It is thus possible to produce, for example, guaiacol from pyrocatechol, but veratrole (1,2-dimethoxybenzene) also forms via an additional (successive) O-methylation reaction of the guaiacol. The processes for preparing alkoxyphenol according to the invention generate at least one compound of the dialkoxybenzene type. This compound can be considered to be an impurity, but also sometimes to be an economically exploitable compound. In view of the potential benefit of the parallel economic exploitation of the alkoxyphenol and of the compounds of the dialkoxybenzene type, it is desired to be able to adjust the synthesis preferentially toward one or other of the compounds according to market demand, i.e. to be able to form to a greater or lesser extent the compound of the dialkoxybenzene type compared with the alkoxyphenol, and vice versa. For example, veratrole can today be exploited separately from guaiacol. Thus, the invention aims to provide a process for producing at least one alkoxyphenol from at least one hydroxyphenol which makes it possible to modulate or adjust the production of the dialkoxybenzene/alkoxyphenol ratio.

An aim of the present invention is in particular to form the dialkoxybenzene compound, such as 1,2-dimethoxybenzene (veratrole), 1,2-diethoxybenzene, 1,4-dimethoxybenzene (PDMB), or 1,4-diethoxybenzene, during the synthesis of alkoxyphenol, such as guaiacol, guaethol, 4-methoxyphenol (PMP) and/or 4-ethoxyphenol (PEP), according to a ratio which meets the isolated needs of the market, i.e. according to a dialkoxybenzene/alkoxyphenol ratio of between 0.001 and 0.9, while limiting the costs of an industrial production. An aim of the invention is in particular to provide such a process while at the same time maximizing the conversion of the starting hydroxyphenol.

Moreover, in order to exploit the highly pure alkoxyphenol compound, it is in particular necessary to separate the latter from the dialkoxybenzene formed. An aim of the present invention is also to remove the dialkoxybenzene compound formed after production of at least one alkoxyphenol from at least one hydroxyphenol. Generally, a dialkoxybenzene compound is difficult to separate from an alkoxyphenol compound. This therefore makes it difficult to obtain the exploitable alkoxyphenol, i.e. alkoxyphenol which is separated in particular from the dialkoxybenzene formed, with a satisfactory degree of purity, while at the same time maintaining industrial production costs which are acceptable for the market.

These problems arise more especially during the production of vanillin (VA) or of ethylvanillin (EVA) from ortho-hydroxyphenol (or pyrocatechol, termed "PC" in the present invention or else called catechol, or pyrocatechin) since the "dialkoxylated" impurity of guaiacol (GA) or of guaethol (GE), such as, in particular, 1,2-dimethoxybenzene (or veratrole) and/or 1,2-diethoxybenzene, is very difficult to separate from GA and/or GE. The compounds of the dialkoxybenzene type, such as veratrole, accumulate during the synthesis of alkoxyhydroxybenzaldehydes since they do not react with glyoxylic acid. It is therefore important to be able to separate or remove the dialkoxybenzene compound from the alkoxyphenol production stream, and therefore also during the production of alkoxyhydroxybenzaldehydes.

The same problems arise in terms of performance and quality of the reaction for O-alkylation of hydroquinone to PMP. It is desired to modulate the PDMB/PMP ratio and to remove the dialkoxylated compound 1,4-dimethoxybenzene (PDMB) from the PMP formed.

Thus, an aim of the invention is also to provide a process for producing, from at least one hydroxyphenol, at least one alkoxyphenol of high purity from the viewpoint of the unwanted presence of dialkoxybenzene compound(s).

Moreover, the production of vanillin and/or of ethylvanillin requires improvement as a whole, in particular starting from the precursor represented by pyrocatechol. This is another independent aim of the process of the invention, as is the control of the amount of veratrole and/or of 1,2-diethoxybenzene produced during a process for synthesizing vanillin and/or ethylvanillin from pyrocatechol.

SUMMARY OF THE INVENTION

The present invention makes it possible to produce the alkoxyphenol compound industrially with a good yield, a low production of impurities and/or efficient removal thereof, and a high hydroxyphenol conversion, while at the same time limiting the costs of an industrial production.

The present invention makes it possible to modulate or adjust the dialkoxybenzene/alkoxyphenol ratio between certain values in order to produce the two compounds according to amounts which meet the momentary needs of the market.

The present invention also makes it possible to remove the dialkoxylated compound formed during the alkoxyphenol production.

The synthesis of alkoxyphenol from hydroxyphenol is known, whether in the gas phase or in a multiphase medium by O-alkylation using an O-alkylating agent. In a multiphase medium, it is also known that the base/alkylating agent ratio and the alkylating agent/hydroxyphenol ratio make it possible to influence the dialkoxybenzene/alkoxyphenol ratio. These ratios directly influence the reaction performance levels, i.e. the degree of conversion of the reagents, the yields of the products formed, and in particular of alkoxyphenol and/or of dialkoxybenzene, and the selectivity of the products obtained, in particular the dialkoxybenzene/alkoxyphenol ratio.

The inventors have discovered, surprisingly, that a medium comprising at least one liquid-liquid phase, and in particular in a three-phase medium, the amount of organic solvent also makes it possible to modulate or adjust the dialkoxybenzene/alkoxyphenol ratio while at the same time preserving very satisfactory, or even optimal, industrial conditions in terms of hydroxyphenol conversion and of yields of the various products. The prior art is, to the inventors' knowledge, silent regarding any influence of the amount of organic solvent on the dialkoxybenzene/alkoxyphenol ratio. It has been noted in the context of the present invention that the amount of organic solvent normally used according to the prior art has no influence on the dialkoxybenzene/alkoxyphenol ratio. However, it has been noted experimentally, surprisingly, by the inventors that, below a certain amount of organic solvent per mole of hydroxyphenol under defined reaction conditions, the amount of organic solvent influences the dialkoxybenzene/alkoxyphenol ratio, such that it is possible to modulate or adjust this ratio according to the market demands and thus to independently exploit the dialkoxybenzene and alkoxyphenol compounds, after separation, while at the same time minimizing the reserves of the compound in excess with respect to the market needs.

The invention does not broach the separation and the exploitation of the dialkoxybenzene compound.

The invention thus relates to a process for producing alkoxyphenol from hydroxyphenol, comprising a reaction for O-alkylation of at least one hydroxyphenol to give at least one alkoxyphenol, said reaction being carried out using an O-alkylating agent, an aqueous solvent comprising a Bröensted base, and an organic solvent, with a base/O-alkylating agent ratio of between 0.5 and 1.5 in moles of base per mole of O-alkylating agent, an O-alkylating agent/hydroxyphenol ratio of between 0.5 and 2 mol of O-alkylating agent per mole of hydroxyphenol, and an organic solvent/hydroxyphenol ratio of less than 280 ml, preferably of between 10 and 250 ml, and more preferably of between 50 and 150 ml of organic solvent per mole of hydroxyphenol.

The base/O-alkylating agent, O-alkylating agent/hydroxyphenol, and organic solvent/hydroxyphenol ratios according to the invention make it possible to adjust the yield of alkoxyphenol compound and/or of dialkoxybenzene compound, and to adjust the hydroxyphenol conversion, and thus to optimize them. It is preferred for the amount of organic solvent used to be less than or equal to the maximum amount of organic solvent influencing the dialkoxyphenol/alkoxyphenol ratio. The maximum amount of organic solvent influencing the dialkoxyphenol/alkoxyphenol ratio depends on the solvent itself and on the precise reaction conditions used. It is preferred for the amount of solvent used to be less than 280 ml, preferably than 250 ml, and more preferably than 150 ml, per mole of hydroxyphenol.

The invention thus relates to a process for producing guaiacol and/or guaethol from pyrocatechol or for producing para-methoxyphenol and/or para-ethoxyphenol from hydroquinone, by O-methylation and/or O-ethylation of one of the hydroxyl groups of the pyrocatechol or of the hydroquinone.

The present invention also relates to a process for producing alkoxyhydroxybenzaldehyde from hydroxyphenol, comprising a reaction for O-alkylation of at least one hydroxyphenol to give at least one alkoxyphenol, said reaction being carried out using an O-alkylating agent, an aqueous solvent comprising a Bröensted base, and an organic solvent, with a base/O-alkylating agent ratio of between 0.5 and 1.5 in moles of base per mole of O-alkylating agent, an O-alkylating agent/hydroxyphenol ratio of between 0.5 and 2 mol of O-alkylating agent per mole of hydroxyphenol, and an organic solvent/hydroxyphenol ratio of less than 280 ml, preferably of between 10 and 250 ml, and more preferably between 50 and 150 ml of organic solvent per mole of hydroxyphenol, and said process comprising a reaction which introduces an aldehyde function on the alkoxyphenol so as to obtain the corresponding alkoxyhydroxybenzaldehyde, preferably by means of a condensation reaction between the alkoxyphenol and glyoxylic acid, and then oxidation of the compound formed.

The present invention relates independently to a process for producing vanillin and/or ethylvanillin from pyrocatechol, comprising a reaction for O-methylation and/or O-ethylation of the pyrocatechol to give guaiacol and/or guaethol, said reaction being carried out using an O-alkylating agent, an aqueous solvent comprising a Bröensted base, and an organic solvent, with a base/O-alkylating agent ratio, an O-alkylating agent/hydroxyphenol ratio and an organic solvent/hydroxyphenol ratio as defined above, said process comprising a reaction which introduces an aldehyde function on the guaiacol and/or the guaethol so as to obtain vanillin and/or ethylvanillin, preferably by means of a condensation reaction between the guaiacol and/or the guaethol and glyoxylic acid, and then oxidation of the condensation product. This specific sequence makes it possible to produce vanillin and/or ethylvanillin industrially with a good yield, a low production of impurities and/or efficient removal thereof, and a high pyrocatechol conversion.

Figure 1:
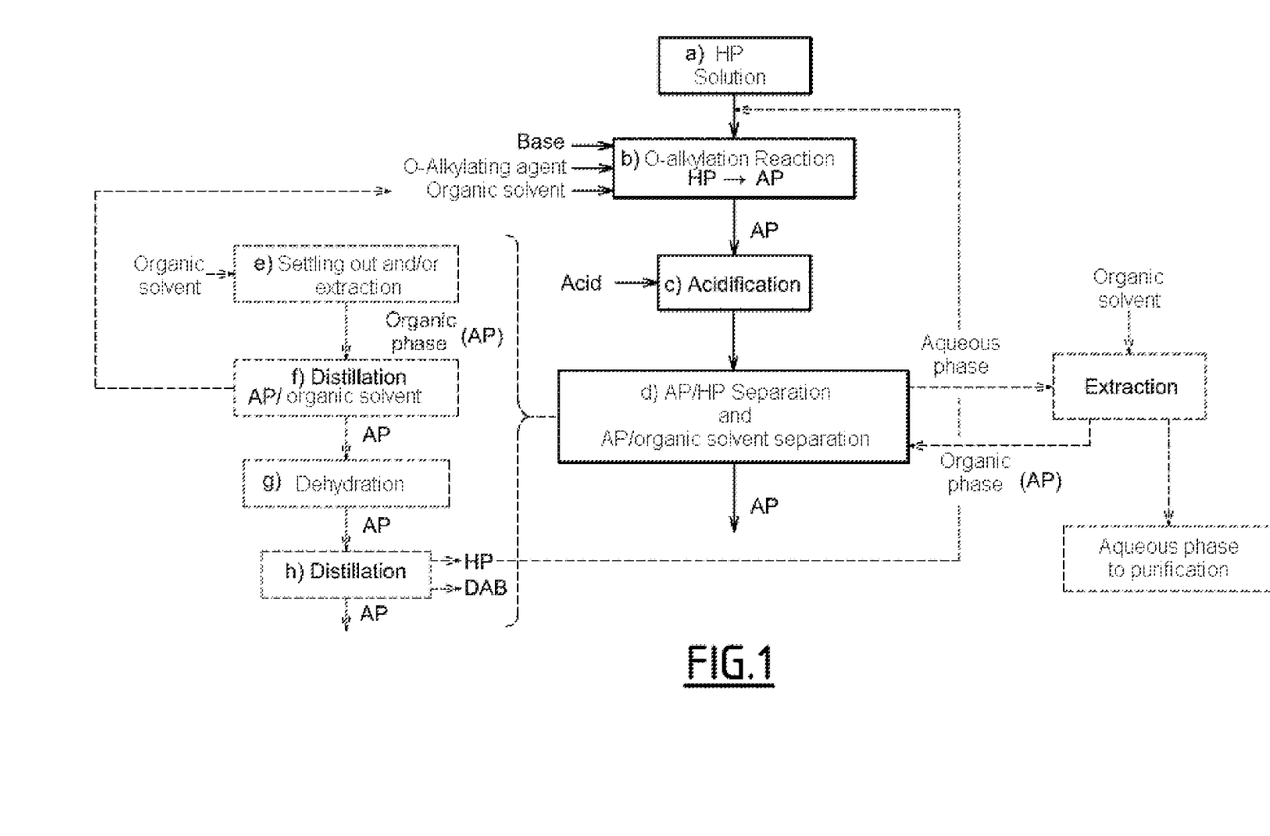
FIG. 1 represents a block diagram of a preferred variant of the process for producing alkoxyphenol from hydroxyphenol.
Figure 2:
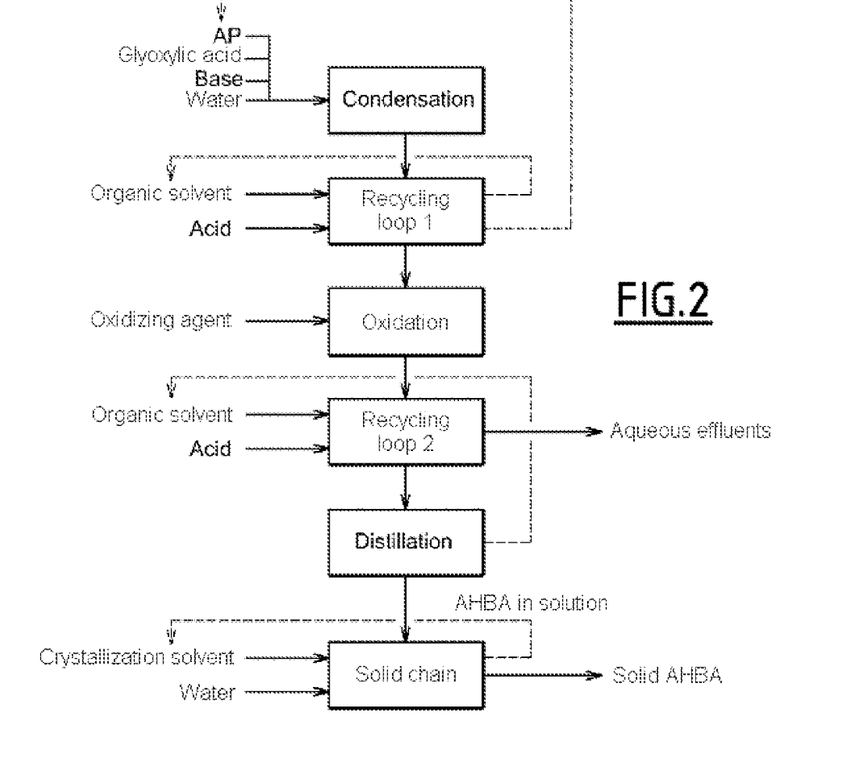
FIG. 2 represents a block diagram of a preferred variant of the production of alkoxyhydroxybenzaldehyde from alkoxyphenol.
Figure 3:
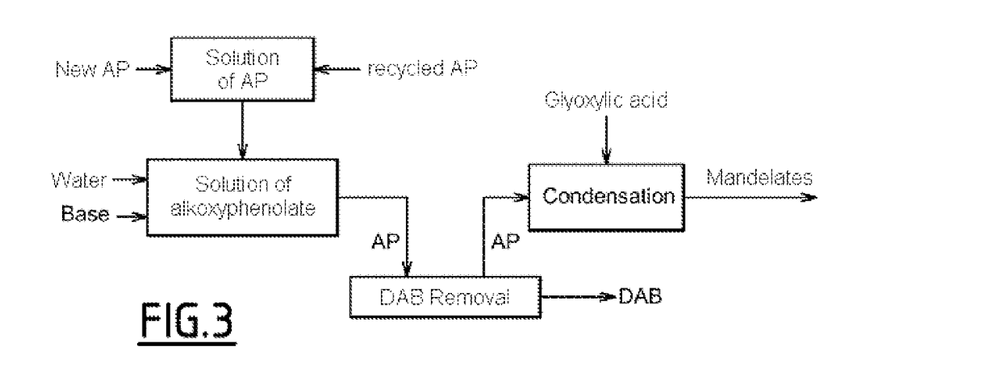
FIG. 3 represents a block diagram according to a preferred variant comprising the removal of a dialkoxybenzene compound prior to the reaction of the alkoxyphenol with glyoxylic acid.

The dashed lines represent, in particular, preferred variants of the process of the invention.

DETAILED DESCRIPTION OF THE INVENTION

The process of the invention applies quite particularly to the production of alkoxyhydroxyphenols such as guaiacol and/or guaethol, or 1,4-methoxyphenol (para-methoxyphenol or PMP) and/or 1,4-ethoxyphenol (para-ethoxyphenol or PEP), but it is also suitable for other alkoxyhydroxyphenols.

The process of the invention applies quite particularly to vanillin and to ethylvanillin, but it is also suitable for other aromatic aldehydes.

The term "hydroxyphenol" is intended to mean at least one compound of benzene type, which is substituted or unsubstituted, comprising two hydroxyl groups. The hydroxyphenol may be substituted, for example, with one or more groups selected from: hydroxyl, alkyl, alkoxy, halogen, nitro and aryl, the groups comprising carbon atoms possibly comprising one or more heteroatoms, in particular selected from O, N and S. It corresponds more particularly to formula (I) below:

(I)

in said formula (I):
the $R_1$ group(s), which may be identical or different, represent a hydrogen atom, a hydroxyl group, or an alkyl or alkoxy group,
n is an integer from 0 to 3.

The respective position of the two hydroxyl groups of formula (I) is not therefore fixed.

They may be in the ortho, meta or para position.

Among the compounds of formula (I), mention may be made of pyrocatechol ("PC" or ortho-hydroxyphenol), resorcin ("RS" or meta-hydroxyphenol) and hydroquinone ("HQ" or para-hydroxyphenol), which are preferred for the process according to the invention.

In the context of the invention, the term "alkyl" is intended to mean a linear or branched hydrocarbon-based chain having from 1 to 12 carbon atoms and preferably from 1 to 4 carbon atoms. Preferred examples of alkyl groups are methyl, ethyl, propyl, isopropyl and tert-butyl groups.

The term "alkoxy" is intended to mean an —O-alkyl group in which the term "alkyl" has the meaning given above. Preferred examples of alkoxy groups are methoxy or ethoxy groups.

The term "alkoxyphenol" is intended to mean at least one compound of benzene type comprising a hydroxyl group and an alkoxy (or O-alkyl) group. It corresponds more particularly to the formula (II) below:

(II)

in said formula (II):
R represents an alkyl group, preferably comprising from 1 to 4 carbon atoms, covalently bonded to the oxygen atom;
$R_1$ and n are as defined above with reference to the compound of formula (I).

The alkoxyphenol compounds are produced from the corresponding hydroxyphenol compound, i.e. the R group, provided by an O-alkylating agent, replaces a hydrogen of one of the hydroxyl groups of the starting hydroxyphenol compound. This reaction is called an O-alkylation reaction.

Mention may in particular be made of guaiacol, guaethol, para-methoxyphenol (PMP) and para-ethoxyphenol (PEP).

The term "alkoxyhydroxybenzaldehyde" is intended to mean at least one phenyl compound comprising a hydroxyl group, an alkoxy (or O-alkyl) group, and a formyl group. It corresponds more particularly to the formula (III) below:

(III)

R, $R_1$ and n are as defined above with reference to the compound of formula (I).

The alkoxyhydroxybenzaldehyde preferentially used in the process of the invention corresponds to the formula (III) in which R represents a methyl or ethyl group and n=0.

As more specific examples of alkoxyhydroxybenzaldehyde, mention may in particular be made of:
vanillin,
ethylvanillin (3-ethoxy-4-hydroxybenzaldehyde),
isovanillin (3-hydroxy-4-methoxybenzaldehyde),
o-vanillin (2-hydroxy-3-methoxybenzaldehyde),
syringic aldehyde (3,5-dimethoxy-4-hydroxybenzaldehyde).

O-Alkylation Reaction

According to the present invention, the hydroxyphenol compound can be converted into monoalkoxylated derivatives, i.e. into alkoxyphenol, by reaction with an O-alkylating agent.

The O-alkylating agent is advantageously selected from compounds which provide an alkyl group as a replacement for the hydrogen atom bonded to the oxygen of the hydroxyphenol compound. Among the various O-alkylating agents, mention may in particular be made of methylating agents and ethylating agents which make it possible to give the corresponding methoxylated and/or ethoxylated compounds.

According to one variant of the invention, the pyrocatechol, the resorcinol or the hydroquinone is converted to the monoalkyl ether thereof by reacting the hydroxyphenol with an alkyl chloride, preferably having from 1 to 4 carbon atoms.

According to one variant, the process of the present invention consists of the production of guaiacol and/or of guaethol from pyrocatechol or the production of para-methoxyphenol and/or of para-ethoxyphenol from hydroquinone, by O-methylation and/or O-ethylation of one of the hydroxyl groups of the pyrocatechol or of the hydroquinone.

Advantageously, the hydroxyphenol is introduced into the alkylation reactor in the form of an aqueous solution.

According to one preferred variant of the invention, the reaction is carried out in a gas-liquid-liquid three-phase medium. According to this variant, the O-alkylating agent is present at least in the gas phase (G/L/L three-phase reaction). The O-alkylating agent is preferably selected from an alkyl halide and preferably a methyl, ethyl, propyl, isopropyl, butyl, isobutyl, tertiary butyl, amyl, sec-amyl, isoamyl or amyl chloride or bromide. The pressure of the O-alkylation reaction is advantageously between 3 and 15 bar, and preferably between 5 and 10 bar. The invention also covers the presence of another phase, for instance the presence of one or more solids, such as one or more supported catalysts.

According to another embodiment, the O-alkylating agent is present at least in solid form (S/L/L three-phase reaction). The O-alkylating agent is preferably selected from an alkyl carbonate or an alkyl sulfate, and preferably from dimethyl sulfate, dimethyl carbonate, diethyl sulfate, diethyl carbonate, and any mixture thereof.

For the O-alkylation reaction, the basic agent (or base) is preferably selected from: an alkali metal or alkaline-earth metal hydroxide, an ammonium hydroxide and an alkylammonium hydroxide, and preferably from sodium hydroxide, potassium hydroxide and an alkali metal carbonate or bicarbonate, and preferably a sodium or potassium carbonate, and any mixture thereof.

An O-alkylating agent/hydroxyphenol ratio of between 0.5 and 2 mol of O-alkylating agent per mole of hydroxyphenol, and more preferably of between 0.7 and 1.7, is preferably used.

The amount of water added can be quite high and can range from 0.5 mol of water per mole of hydroxyphenol up to 30 mol of water per mole of hydroxyphenol, and is preferably 4 to 30 mol of water per mole of hydroxyphenol. However, it is not solely important to adjust the amount of water according to the amount of hydroxyphenol. Advantageously, the O-alkylation of the hydroxyphenol to give alkoxyphenol in a basic multiphase medium has an organic solvent/water ratio, by weight/weight, of less than 1.5, and preferably less than 1.2, and more preferably ranging from 0.05 to 0.8.

For the O-alkylation reaction, the organic solvent is selected so as to extract the alkoxyphenol compound from the aqueous phase as said compound is formed and to partially solubilize the O-alkylating agent, and to thus limit the formation of the dialkoxybenzene compound in order to preserve a satisfactory dialkoxybenzene/alkoxyphenol ratio. The organic solvent is also selected so as to partially solubilize the O-alkylating agent in the organic solvent and to thus limit the degradation of the O-alkylating agent on contact with the base present in aqueous solution, in particular so as to increase the O-alkylation yield of alkoxyphenol compound. The organic solvent is preferably selected from: a linear, branched or unbranched, or cyclic alkane comprising from 5 to 10 carbon atoms, for example cyclopentane, cyclohexane, methylcyclohexane, cycloheptane, n-heptane, octane, a halogenated alkane such as dichloroethylene or dichloropropylene, an aliphatic alcohol, such as methanol, an organic solvent comprising from 2 to 10 carbon atoms and an ether function, for example diethyl ether, diisopropyl ether, methyl (tert-butyl) ether, a solvent comprising from 2 to 10 carbon atoms and a ketone function, for example acetone and diethyl ketone, methyl isobutyl ketone, a polyol, such as a glycol or a poly (ethylene glycol), an aromatic solvent comprising from 5 to 12 carbon atoms, for example toluene, xylenes, benzene and ethylbenzene. Solvents of food quality may be used.

It is known, moreover, how to prepare compounds of hydroxyphenol type. The hydroxyphenol is prepared, for example, by hydroxylation of phenol. The hydroxyphenol is advantageously added in liquid form. Thus, the hydroxyphenol is preferably dissolved in an aqueous medium prior to the O-alkylation reaction.

According to one preferred variant, the reactor in which the O-alkylation reaction is carried out comprises a means for introducing a solution of at least one hydroxyphenol into the reactor, a means for introducing at least one O-alkylating agent into the reactor, a means for introducing at least one basic aqueous solution into the reactor, a means for introducing at least one organic solvent into the reactor, and at least one means for removing the reaction mixture comprising in particular the alkoxyphenol and the dialkoxybenzene formed. According to one variant, water is introduced into the reactor in addition to the water present in the base introduced (basic solution) and to the hydroxyphenol (hydroxyphenol solution).

The reaction conditions fixed by the process of the present invention make it possible very advantageously to obtain, in particular for the synthesis of guaiacol, a veratrole/guaiacol ratio of between 0.001 and 0.9, while at the same time maximizing the degree of conversion of the catechol, industrially, while limiting the production costs, and the impurities formed.

The reaction conditions fixed by the process of the present invention make it possible very advantageously to obtain, in particular for the synthesis of PMP, a PDMB/PMP ratio of between 0.001 and 0.9, while at the same time maximizing the degree of conversion of hydroquinone, industrially, while limiting the production costs, and the impurities form.

The reaction gives the alkoxyphenol with a very good yield.

The temperature of the O-alkylation reaction is preferably between 80 and 150° C. and preferably between 100 and 140° C.

The reaction is preferably carried out in an autoclave.

The pH of the aqueous phase during the O-alkylation reaction is preferably between 8 and 12.

The residence time or the reaction time is between 15 minutes and 3 hours and preferably between 30 and 90 minutes.

The invention covers in particular the production of guaiacol and/or of guaethol for use thereof in the synthesis of vanillin and/or of ethylvanillin. Reference is therefore in particular made to the production of guaiacol (GA) and/or of guaethol (GE), but the invention covers the production of any alkoxyphenol and mixtures thereof, and in particular the production of para-methoxyphenol (PMP) and/or para-ethoxyphenol (PEP). The invention specifically covers the production of guaiacol and/or of guaethol from pyrocatechol.

More particularly, and reference may be made to FIG. 1, the process for producing the alkoxyphenol (advantageously GA and/or GE or PMP and/or PEP) comprises the following steps:

(a) optional pre-dissolution of the solid hydroxyphenol (advantageously catechol (PC) or hydroquinone (HQ)) in an aqueous medium;

(b) O-alkylation of hydroxyphenol (PC ou HQ) to give alkoxyphenol (advantageously GA and/or GE or PMP and/or PEP) in a basic multiphase (preferably G/L/L three-phase) medium;

(c) acidification of the resulting mixture;

(d) separation of the alkoxyphenol from the hydroxyphenol, and separation of the alkoxyphenol from the organic solvent, and recovery at least of the alkoxyphenol compound.

These steps can be carried out continuously or semi-continuously or batchwise.

In the interests of simplicity, no reference is made here to the dialkoxybenzene compound formed. Dialkoxybenzene is formed when alkoxyphenol is synthesized.

The compound of main interest, i.e. the alkoxyphenol (advantageously the GA and/or GE or PMP and/or PEP) is essentially in the organic phase. The invention makes it possible to prepare two principal qualities: in particular guaiacol and/or guaethol in liquid form, and guaiacol and/or guaethol in solid form.

The acidification (step (c)) of the reaction medium after O-alkylation is preferably carried out by adding an inorganic acid. Acidification is preferably carried out with sulfuric acid. The aim of this acidification is to transfer the alkoxyphenolate formed (advantageously guaiacolate and/or guaetholate or para-methoxyphenolate and/or para-ethoxyphenolate), present in the basic aqueous phase, into the organic phase in the form of alkoxyphenol (guaiacol and/or guaethol).

The step of separation (step d) of the alkoxyphenol from the hydroxyphenol, and of separation of the alkoxyphenol from the organic solvent, preferably comprises a settling out of the acidified reaction medium resulting from the O-alkylation and a separation of the organic and aqueous phases. The organic phase, i.e. the organic solvent-alkoxyphenol mixture, is distilled so as to separate the alkoxyphenol compound from the organic solvent, and is then dehydrated (removal of the water). According to one preferred variant, the organic solvent used in step d) may be identical to the one used in step b) and may therefore advantageously be recycled so as to be used in the O-alkylation step and/or in the aqueous-phase treatment step.

The aqueous phase may advantageously be treated so as to recover the hydroxyphenol (in particular PC or HQ), and the possible residues of alkoxyphenol compound (GA and/or GE or PMP and/or PEP). This treatment preferably comprises an extraction of the aqueous phase with an organic solvent, preferably with the same solvent as the one used for the O-alkylation reaction. The organic phase obtained following this separation may advantageously be added to the organic phase obtained after separation of the aqueous phase.

The separation according to step (d) of the process of the invention advantageously comprises the following steps:

(e) settling out of the aqueous and organic phases and/or extraction of the residual alkoxyphenol (GA and/or GE or PMP and/or PEP) in the aqueous phase with an organic solvent;

(f) distillation of the organic phase comprising the organic solvent and the alkoxyphenol (advantageously GA and/or GE or PMP and/or PEP) and recycling of the organic solvent;

(g) removal of the water (dehydration) from the mixture containing the alkoxyphenol (advantageously GA and/or GE or PMP and/or PEP);

(h) distillation of the reaction crude so as to separate the alkoxyphenol compound, the dialkoxybenzene compound and the tars (cf. below step h).

Advantageously, steps e) to g) are carried out continuously, with the exception optionally of the settling out.

After the dehydration step (g), the process of the invention may comprise a "discontinuous" zone comprising a step of distillation of the alkoxyphenol (advantageously GA and/or GE or PMP and/or PEP) so as to purify it.

The process is therefore advantageously continuous, with the exclusion optionally of the distillation of the alkoxyphenol (advantageously GA and/or GE or PMP and/or PEP).

The process may comprise a step h) of distillation of the reaction crude, i.e. the organic phase, the organic solvent of which has been removed, is distilled so as to separate the alkoxyphenol compound, the dialkoxybenzene compound and the tars. The latter may be treated so as to recover the hydroxyphenol which has not reacted during the reaction, which can thus be recycled. The dehydration (g) of the crude alkoxyphenol (GA and/or GE or PMP and/or PEP) is therefore preferably followed by a distillation (step h) in order to separate the alkoxyphenol compound (GA and/or GE or PMP and/or PEP) from the other organic compounds present, such as the possible residues of the hydroxyphenol compounds (unreacted reagent) and dialkoxybenzene, and from the tars (dimers, trimers, oligomers, and other organic compounds of very high molecular weight).

The hydroxyphenol (unreacted reagent) is more preferably separated from the tars by means of a treatment known to those skilled in the art. The hydroxyphenol is preferably recycled for the O-alkylation step. The invention makes it possible to maximize the conversion of the hydroxyphenol while at the same time minimizing the production costs.

The dialkoxybenzene (veratrole and/or 1,2-diethyoxybenzene, or 1,4-dimethyoxybenzene and/or 1,4-diethyoxybenzene) can advantageously be exploited by treating it by means of an additional purification step, known to those skilled in the art, such as a distillation, or a step of washing procedure(s), or other purification techniques. In accordance with the invention, the amount of organic solvent used should preferably be less than or equal to the maximum amount of organic solvent influencing the dialkoxyphenol/alkoxyphenol ratio in order to be able to vary the dialkoxybenzene/alkoxyphenol ratio and to limit the dialkoxybenzene and alkoxyphenol reserves in excess with respect to the market needs.

The invention also covers the production of at least one alkoxyhydroxybenzaldehyde from hydroxyphenol.

Synthesis of alkoxyhydroxybenzaldehyde

The process according to the invention makes it possible to produce an alkoxyhydroxybenzaldehyde by adding an aldehyde function to the abovementioned alkoxyphenol compound.

The process according to the invention makes it possible to produce in particular vanillin and/or ethylvanillin from guaiacol and/or guaethol. The guaiacol/guaethol mixture is obtained in any proportions. The GA/GE ratio depends on the O-alkylation conditions. This GA/GE weight ratio may, for example, range from 0.1/100 to 100/1. The vanillin/ethylvanillin weight ratio preferably ranges from 80/20 to 40/60, or preferably from 80/20 to 45/55. According to one variant, the vanillin/ethylvanillin molar ratio is at least equal to 2. Preferably, the proportion of vanillin by weight is between 65% and 72%, and preferably between 60% and 70%, and the proportion of ethylvanillin is between 28% and 35%, and preferably between 30% and 33% by weight.

Reference is made to the alkoxyphenol, guaiacol and guaethol compounds, and to the corresponding alkoxyhydroxybenzaldehydes independently of their salified or nonsalified form. When reference is explicitly made to the salt, this makes it possible to describe a particular detail regarding this aspect. Those skilled in the art are able to know when they are in the presence of the salified or nonsalified compound, in particular in the light of the cited literature and of their general knowledge.

The aldehyde function is advantageously provided according to two main reactions, namely a condensation of the alkoxyphenol compound with glyoxylic acid and the oxidation of the compound resulting from the condensation reaction.

According to one preferred embodiment, the process of the invention also comprises the following steps:

condensation of the alkoxyphenol compound with glyoxylic acid so as to obtain the corresponding mandelic compound;

separation of the alkoxyphenol compound from the solution containing the mandelic compound, preferably with recycling of the alkoxyphenol compound;

oxidation of the mandelic compound so as to obtain the alkoxyhydroxybenzaldehyde;

separation of the alkoxyhydroxybenzaldehyde by extraction with an organic solvent, then separation of the alkoxyhydroxybenzaldehyde from the organic solvent, preferably with recycling of the alkoxyhydroxybenzaldehyde extraction organic solvent; and recovery of the alkoxyhydroxybenzaldehyde, optionally in solid form.

When "mandelic", "vanillin" or "ethylvanillin" is mentioned without further information, the para-mandelic compound, para-vanillin or ethyl-para-vanillin is respectively targeted, unless otherwise indicated.

The para-mandelic compounds (formula (IV)), in particular the production of para-vanillin, have the following formulae:

(IV)

mandelic compound of para-vanillin

Preferably, the steps and their sequence are carried out continuously, with the exception of a few steps as during the separation of the compounds.

The reactions for condensation of the alkoxyphenols, and in particular of guaiacol, with glyoxylic acid are described in the literature. Mention will quite particularly be made of patents EP 0 578 550, WO 99/65853 and WO 09077383, to which reference is made for the production of the compounds of the invention.

The sequence of the above steps can be carried out according to the following reactions according to the example guaiacol:

Condensation of guaiacol and of glyoxylic acid so as to form para-mandelic acid:

guaiacol+glyoxylic acid+NaOH→guaiacolate+mandelate(phenate)+H$_2$O

Acidification so as to recover the unreacted guaiacol:

guaiacolate+mandelate(phenate)+→guaiacol+mandelate+Na$_2$SO$_4$H$_2$SO$_4$

Oxidation of the para-mandelic acid so as to form para-vanillin:

mandelate+NaOH+O$_2$→vanillate+Na$_2$CO$_3$+H$_2$O

Acidification so as to form vanillin:

vanillate+Na$_2$CO$_3$+H$_2$SO$_4$→VA+CO$_2$+Na$_2$SO$_4$

During the separation of the mixture, whether it is of the alkoxyphenol or of the alkoxyhydroxybenzaldehyde, having resulted in their formation, a recycling, also called a loop, is preferably carried out. Thus, in the present invention, reference is made to "recycling loop 1" when referring to the recycling of the excess alkoxyphenol during the condensation reaction, and to "recycling loop 2" when referring to the recycling of the alkoxyhydroxybenzaldehyde extraction solvent, during the separation steps.

Once separated, the alkoxyhydroxybenzaldehyde may be treated so as to obtain it in solid purified form; reference is made in the present invention to "solid chain". This treatment can typically implement the steps of crystallization, pulling dry, and drying, or flaking. Among these steps, some, like the pulling dry, may not be carried out continuously. Thus, the process is preferably continuous, with the exclusion of the pulling dry.

The vanillin and/or the ethylvanillin thus obtained may in particular be used as a flavoring in industry, for instance in the food, pharmaceutical or cosmetics industry, in particular for example for manufacturing fragrances.

The vanillin and/or the ethylvanillin may also be used as a synthesis intermediate, for example for the production of veratric aldehyde (3,4-dimethoxybenzaldehyde) and/or 3,4-diethoxybenzaldehyde.

In this context, if the process relates to the simultaneous production of vanillin and of ethylvanillin, it is possible either to synthesize the vanillin and ethylvanillin according to the same stream, from a stream comprising guaiacol and guaethol, themselves prepared from catechol by simultaneous reaction with an O-methylating agent and an O-ethylating agent; or to synthesize guaiacol and guaethol separately and then to mix them before the condensation step so as to synthesize the vanillin and ethylvanillin according to the same stream; or to synthesize the mandelic compounds separately via separate reactions of the guaiacol and of the guaethol with glyoxylic acid and then to mix the corresponding mandelic compounds before the oxidation step; or to synthesize the vanillin and ethylvanillin separately and then to mix them, for example before the crystallization.

Thus, it is possible to represent the reaction scheme according to FIG. 2 which advantageously comprises the following steps:

succession of steps a) to d) (and preferably including steps e) to h) described above in particular with reference to FIG. 1), so as to recover at least one alkoxyphenol;

condensation of the alkoxyphenol (AP) compound with glyoxylic acid so as to obtain the corresponding mandelic compound, after the addition of water, of glyoxylic acid and of a base;

separation of the alkoxyphenol compound from the solution containing the corresponding mandelic compound, after the addition of an organic solvent and of an acid, preferably with recycling of the alkoxyphenol compound;

oxidation of the mandelic compound by reaction with an oxidizing agent introduced so as to obtain the corresponding alkoxyhydroxybenzaldehyde;

separation of the alkoxyhydroxybenzaldehyde by extraction after the addition of an organic solvent and of an acid;

separation of the alkoxyhydroxybenzaldehyde from the organic solvent by distillation, preferably with recycling of the organic solvent; and recovery of the alkoxyhydroxybenzaldehyde (AHBA), optionally in solid form.

Condensation Reaction

According to one advantageous variant, the alkoxyphenol is reacted with glyoxylic acid in the presence of an inorganic base and of an organic base, and preferably NaOH or KOH, and more preferably in the presence of sodium hydroxide (NaOH), or ammonium hydroxide. According to this variant, a mixture of alkyl phenolate and of derivative of the mandelate type is obtained.

The condensation reaction between the alkoxyphenol (in phenolate form) and glyoxylic acid allows the synthesis of the corresponding para-mandelic acid.

The condensation can be carried out in a cascade of stirred reactors. According to one variant, the reaction is carried out in a piston flow reactor, optionally comprising a heat exchanger. Such an embodiment is, for example, described for guaiacol in application WO 09/077383. The condensation reaction between the alkoxyphenol and glyoxylic acid can be carried out in water, in the presence of an alkali metal, said reaction being carried out in a piston flow reactor. It can be carried out in a tubular reactor.

The condensation reaction can advantageously be catalyzed by a quaternary ammonium hydroxide, for instance according to the reaction described in patent application EP 0 578 550.

The condensation reaction can advantageously be carried out in the presence of a dicarboxylic acid, for instance according to the reaction described in patent application WO 99/65853.

Since the alkoxyphenol is usually in excess with respect to the glyoxylic acid, the alkoxyphenol fraction which has not reacted is advantageously recovered from recycling loop 1. This excess reduces the probability of forming compounds of the dimandelic acid type (i.e. compounds resulting from the condensation of two glyoxylic acid molecules with one guaiacol molecule).

Advantageously, firstly, the alkoxyphenol and sodium hydroxide react to form sodium alkoxyphenolate. For example for guaiacol:

Then the alkoxyphenolate reacts with glyoxylic acid to form the corresponding para-mandelate:

These two reactions for preparing the glyoxylate and the guaiacolate can be carried out according to two separate steps. Alternatively, the glyoxylic acid is brought into contact directly with the guaiacolate in the presence of the base.

Alkoxyphenolate Solution

According to one advantageous variant, an alkoxyphenolate solution is prepared. This alkoxyphenolate solution is fed with alkoxyphenol from a storage tank which receives the alkoxyphenol recycled from recycling loop 1 and the new alkoxyphenol. This alkoxyphenolate solution is advantageously introduced into the reactor for the condensation reaction.

All of the (demineralized) water and of an inorganic base (for example sodium hydroxide) required for the reaction are fed into the alkoxyphenolate solution.

The temperature of the reactor for preparing the alkoxyphenolate solution is advantageously maintained at the condensation reaction temperature.

Recycling Loop 1

Recycling loop 1 is the recovery of the alkoxyphenol which has not reacted in the condensation reaction. Thus, loop 1 relates to the separation of the alkoxyphenol compound from the mandelic compounds, which advantageously comprises the following steps:

recovery of a mixture comprising the mandelic compound formed in mandelate form and the unreacted alkoxyphenol in alkoxyphenolate form;

neutralization of the alkoxyphenolate to give the alkoxyphenol, while maintaining the corresponding mandelate in conjugated base (salified) form;

separation of the alkoxyphenol from the mandelate;

introduction of the mandelate into an oxidation reactor; and recycling of the alkoxyphenol, which has not reacted as a reagent, to the condensation reaction.

The reaction medium resulting from the condensation is advantageously neutralized with an inorganic acid, and preferably with sulfuric acid, so as to convert the unreacted alkoxyphenolate into alkoxyphenol under conditions which keep the mandelate in salified form.

The unreacted alkoxyphenol, present in the organic phase, can be separated from the mandelate formed, present in the aqueous phase.

According to one variant, the alkoxyphenol obtained after neutralization can be extracted by extraction via the addition of an organic solvent which solubilizes the alkoxyphenol contained in the aqueous phase. Reference is made here, for example, to the process described for guaiacol in patent FR 2 379 501.

According to one preferred embodiment, the alkoxyphenol contained in the aqueous phase is extracted with an organic solvent. Use is made of an organic solvent which is inert with respect to the mandelate. As solvents which can be used, mention may in particular be made of halogenated or nonhalogenated aliphatic, cycloaliphatic or aromatic hydrocarbons; alcohols; ethers; ketones and nitriles. As aliphatic, cycloaliphatic or aromatic hydrocarbons, mention is more particularly made of heptane, cyclohexane, methylcyclohexane, benzene and toluene; as halogenated aliphatic, cycloaliphatic or aromatic hydrocarbons, mention is more particularly made of dichloromethane, trichloromethane, dichloroethane, chlorobenzene and dichlorobenzenes; as alcohols, mention is more particularly made of methanol, ethanol, propanol, isopropanol and butanol; as ethers, mention is more particularly made of diethyl ether, diisopropyl ether and methyl (tert-butyl) ether; as ketones, mention is more particularly made of acetone, methyl ethyl ketone, methyl isobutyl ketone and diisobutyl ketone; and as nitriles, mention is more particularly made of acetonitrile. A mixture of said solvents may be used. A solvent of food quality may be used.

The mandelate then remains in the aqueous phase, whereas the alkoxyphenol goes into the organic phase.

The alkoxyphenol to be recycled may be contaminated by the presence of organic solvent residues. The presence of organic solvent in the alkoxyphenol results in a significant decrease in the performance levels of the condensation reaction. It is therefore preferable to separate the extraction solvent from the alkoxyphenol before its reintroduction into the alkoxyphenol storage tank.

After separation of the aqueous and organic phases, the alkoxyphenol-organic phase mixture is preferably distilled so as to separate the organic solvent from the alkoxyphenol, and also from tars generally present, in order to recycle the organic solvent.

Other types of separation may be envisioned.

The aqueous phase containing the mandelate is preferably treated so as to remove the residual organic solvent, for example by distillation. The mandelate then feeds the oxidation reaction.

According to one variant, the unreacted alkoxyphenolate can be separated using basic anion exchange resins or an adsorbent resulting in selective binding of the alkoxyphenol and in the recovery of an aqueous stream comprising the mandelic compounds in salified form resulting from the condensation reaction. The stream of the alkoxyphenol in salified form (alkoxyphenolate) bound to the resin or the adsorbent can be separated by means of a resin regeneration treatment or a desorption treatment. Such separation methods are in particular described in patent applications WO 09/141280 and WO 11/039331.

The alkoxyphenol which has not reacted during the condensation reaction is preferably recycled to the feed of the alkoxyphenolate solution.

Removal of the Dialkoxybenzene (Called "DAB") Possibly Present

As was indicated above, the O-alkylation reaction also generates a dialkoxybenzene compound. In the process of the invention, the alkoxyphenol obtained after the O-alkylation reaction is therefore in a mixture with a super alkoxylation (dialkoxylation) compound of the dialkoxybenzene type.

It has in particular been discovered by the inventors that, when veratrole (1,2-dimethoxybenzene) is formed, in particular when guaiacol has been prepared from pyrocatechol, the veratrole accumulates in the guaiacol solution owing to the recycling, but also because it does not react during the condensation reaction with glyoxylic acid.

The veratrole concentration in the guaiacol storage tank (mixture of new+recycled) is variable. Since veratrole does not react in the condensation reactions according to the invention, veratrole therefore has a tendency to accumulate in the guaiacol solution and thus reduces the guaiacol titer in the solution injected into the condensation reactor. In the process of the invention, it is sought to limit the veratrole accumulated in the guaiacol or the guaiacolate solution. Thus, according to one preferred embodiment of the invention, the dialkoxybenzene formed is removed. According to one variant of the process of the invention, the veratrole concentration by weight in the solution comprising AP before the condensation reaction is between 0.01% and 25% and preferably between 0.01% and 10%, and more preferably between 0.01% and 5%, and is generally approximately 2%.

The invention therefore relates to an independently patentable process for producing at least one alkoxyhydroxybenzaldehyde compound from at least one hydroxyphenol compound, said process being characterized in that it comprises:

(i)—the synthesis of at least one alkoxyphenol from at least one hydroxyphenol in the presence of at least one O-alkylating agent;

(ii)—the recovery of at least one alkoxyphenol and of impurities, including a dialkylated compound of the dialkoxybenzene type (also called here "DAB");

(iii)—the separation of the dialkoxybenzene from the alkoxyphenol;

(iv)—the condensation of the alkoxyphenol with glyoxylic acid and the obtaining of the corresponding mandelic compound;

(v)—the oxidation of the mandelic compound to give the corresponding alkoxyhydroxybenzaldehyde; and (vi)—the recovery of the alkoxyhydroxybenzaldehyde optionally in solid form.

In particular, the invention consists of a process for producing at least one alkoxyhydroxybenzaldehyde selected from vanillin (4-hydroxy-3-methoxybenzaldehyde), ethylvanillin (3-ethoxy-4-hydroxybenzaldehyde), and any mixture thereof, from pyrocatechol.

According to one preferred variant, step (i) is carried out in a three-phase medium as described in the invention, including all the variants and embodiments described without any limitation.

According to one preferred embodiment, step (iii) of separation of the dialkoxybenzene from the alkoxyphenol also comprises the preparation of an aqueous solution of alkoxyphenol in salified (phenolate) form, and the separation of the residual dialkoxybenzene from the aqueous mixture comprising the alkoxyphenoate.

According to one preferred variant, illustrated for example according to FIG. 3, the process comprises the following steps:
- preparation of a solution of alkoxyphenol (AP) for example in a mixture made up of a new alkoxyphenol with an alkoxyphenol originating from recycling, said solution of alkoxyphenol also comprising an impurity of the dialkoxybenzene (DAB) type;
- preparation of a solution of alkoxyphenolate by adding water and at least one base to the solution of alkoxyphenol;
- separation of the dialkoxybenzene from the alkoxyphenol;
- optional exploitation of the dialkoxybenzene;
- condensation of the alkoxyphenol with glyoxylic acid and obtaining of the corresponding mandelic compound, which is for example salified (mandelate).

According to one variant, the separation of the dialkoxybenzene from the alkoxyphenol is carried out by distillation or settling out.

Advantageously, the mandelic compounds are obtained in salified form. Thus, the process of the invention comprises a step of neutralization of the salified mandelic compound to give the mandelic compound in acid form.

According to one variant, the hydroxyphenol is pyrocatechol, the alkoxyphenol is the guaiacol obtained in step (i) with a methylating agent, and the dialkoxybenzene is veratrole, and the process also comprises the separation, in step (iii), of the pyrocatechol from the guaiacol and veratrole mixture.

According to one variant, the hydroxyphenol is pyrocatechol, the alkoxyphenol is the guaethol obtained in step (i) with an ethylating agent, and the dialkoxybenzene is 1,2-diethoxybenzene, and the process also comprises the separation, in step (iii), of the pyrocatechol from the guaethol and 1,2-diethoxybenzene mixture.

Advantageously, a part of the alkoxyphenol (alkoxyphenolate) is advantageously diverted to a distillation column intended to limit the dialkoxybenzene content in the guaiacol before the condensation reaction. The dialkoxybenzene is distilled at the top in the form of a dialkoxybenzene-water heteroazeotrope. A temperature at the bottom of the distillation column of between 90 and 120° C. is preferred. This process makes it possible, for example for guaiacol, to limit the veratrole concentration by weight to 0.01% in the guaiacol (or guaiacolate) used for the condensation reaction.

The dialkoxybenzene-water heteroazeotrope is then advantageously separated by settling out or another means of separation.

The bottom of the column (comprising the alkoxyphenolate) is preferably directed to the feed of the condensation reactor so as to cause the alkoxyphenol (alkoxyphenolate) and the glyoxylic acid to react by condensation.

Oxidation of the Mandelic Compounds to Give Alkoxyhydroxybenzaldehyde

The oxidation step allows the conversion of the mandelic compounds into the desired alkoxyhydroxybenzaldehydes. The para-mandelic compound corresponds more particularly to the abovementioned formula (IV). In particular, para-vanillin (called here vanillin) can be produced in vanillate form by oxidation of the corresponding para-mandelic acid.

The alkoxyhydroxybenzaldehyde is obtained by oxidation of the corresponding mandelic compound, preferably in an oxidizing atmosphere, such as $O_2$ or air.

According to one variant, the reaction medium is an alkaline aqueous medium, preferably an inorganic base and more preferably sodium or potassium hydroxide, so as to form the corresponding phenate, and to capture the released $CO_2$, in carbonate form.

The reaction may be carried out continuously or batchwise, for example in a medium strongly diluted in water.

The reaction can be catalyzed. A catalyst of this oxidation reaction may be selected from catalysts comprising at least one metal element selected from the group formed by copper, nickel, cobalt, iron, manganese, and any mixture thereof. By way of examples of inorganic or organic copper compounds, mention may in particular be made, as copper compounds, of cuprous and cupric bromide; cuprous iodide; cuprous and cupric chloride; basic cupric carbonate; cuprous and cupric nitrate; cuprous and cupric sulfate; cuprous sulfite; cuprous and cupric oxide; cupric hydroxide; cuprous and cupric acetate; and cupric trifluoromethyl sulfonate. As specific examples of nickel derivatives, mention may be made of nickel(II) halides, such as nickel(II) chloride, bromide or iodide; nickel(II) sulfate; nickel(II) carbonate; the salts of organic acids comprising from 1 to 18 carbon atoms, such as, in particular, acetate or propionate; nickel(II) complexes, such as nickel(II) acetylacetonate, nickel(II) dichlorobis (triphenylphosphine) or nickel(II) dibromobis(bipyridine); and nickel(0) complexes, such as nickel(0) bis(cycloocta-1,5-diene) or nickel(0) bisdiphenylphosphinoethane. As examples of cobalt-based compounds, mention may in particular be made of cobalt(II) and (III) halides, such as cobalt (II) chloride, bromide or iodide or cobalt(III) chloride, bromide or iodide; cobalt(II) and cobalt(III) sulfate; cobalt(II) carbonate, basic cobalt(II) carbonate; cobalt(II) orthophosphate; cobalt(II) nitrate; cobalt(II) and cobalt(III) oxide; cobalt(II) and cobalt(III) hydroxide; the salts of organic acids comprising from 1 to 18 carbon atoms, such as, in particular, cobalt(II) and cobalt(III) acetate or cobalt(II) propionate; cobalt(II) complexes, such as hexaminecobalt(II) or (III) chloride, hexaminecobalt(II) or (III) sulfate, pentaminecobalt (III) chloride or triethylenediaminecobalt (III) chloride. Use may also be made of iron-based catalytic systems, generally in the form of oxides, of hydroxides or of salts, such as iron(II) and iron(III) chloride, bromide, iodide or fluoride; iron(II) and iron(III) sulfate; iron(II) and iron(III) nitrate; or iron(II) and iron(III) oxide. The oxidation reaction can be catalyzed, for example, by a catalytic system comprising two metal elements selected from the group formed by copper, nickel, cobalt, iron, manganese, and any mixture thereof. The present invention covers in particular the reactions described according to patent application WO 08/148760.

Firstly, the mandelate compound reacts with the base (preferably sodium hydroxide) so as to salify the phenate function of the mandelate compound. Then, the oxidation in an oxidizing medium (preferably in air) produces vanillate and $CO_2$ (trapped in carbonate form).

The oxidation of the para-mandelic compound to give para-vanillin is virtually complete, with very good selectivity.

At the end of the oxidation reaction, the precursor of the alkoxyhydroxybenzaldehyde (vanillin and/or ethylvanillin), i.e. with a hydroxyl group in salified (ionic) form, and various impurities, including tars, are obtained.

In a subsequent step, the acidification of the alkoxyhydroxybenzaldehyde (vanillin and/or ethylvanillin) in the reaction medium is carried out using a strong acid, for example sulfuric acid. It is then necessary to recover the noble product, namely the alkoxyhydroxybenzaldehyde (vanillin and/or ethylvanillin), in the presence of tars according to a process which is both friendly to the integrity of the products to be separated while at the same time being economical, and easy to carry out in industrial devices, quite particularly in those which operate continuously. To separate the alkoxyhydroxybenzaldehyde (vanillin and/or ethylvanillin) from the crude reaction mixture, a known method consists in carrying out the extraction thereof using an organic solvent.

Advantageously, the process comprises:
the separation of the alkoxyhydroxybenzaldehyde from the reaction mixture by extraction with an organic solvent; and
the recovery and the recycling of the organic solvent used for the extraction.

Recycling Loop 2

Recycling loop 2 covers the conversion of the alkoxybenzaldehyde hydroxylate (vanillate and/or ethyl vanillate) obtained after the oxidation reaction to give the corresponding alkoxyhydroxybenzaldehyde, and the recovery and the recycling of the solvent used for the extraction of the alkoxyhydroxybenzaldehyde (vanillin and/or ethylvanillin) from the mixture resulting from the oxidation reaction. The invention covers in particular the production of vanillin and/or of ethylvanillin.

The reaction medium resulting from the oxidation is acidified with an acidic medium, preferably containing an inorganic acid, and for example sulfuric acid, or hydrochloric acid, so as to convert the alkoxyhydroxybenzaldehyde salt into alkoxyhydroxybenzaldehyde.

According to one preferred embodiment, the alkoxyhydroxybenzaldehyde contained in the aqueous phase is extracted with an organic solvent which solubilizes the alkoxyhydroxybenzaldehyde contained in the aqueous phase. Use is made of an organic solvent which is inert with respect to the alkoxyhydroxybenzaldehyde. As solvents which can be used, mention may in particular be made of halogenated or nonhalogenated aliphatic, cycloaliphatic or aromatic hydrocarbons; alcohols; ethers; ketones and nitriles. As aliphatic, cycloaliphatic or aromatic hydrocarbons, mention is more particularly made of heptane, cyclohexane, methylcyclohexane, benzene and toluene; as halogenated aliphatic, cycloaliphatic or aromatic hydrocarbons, mention is more particularly made of dichloromethane, trichloromethane, dichloroethane, chlorobenzene and dichlorobenzenes; as alcohols, mention is more particularly made of methanol, ethanol, propanol, isopropanol and butanol; as ethers, mention is more particularly made of diethyl ether, diisopropyl ether and methyl (tert-butyl) ether; as ketones, mention is more particularly made of acetone, methyl ethyl ketone, methyl isobutyl ketone and diisobutyl ketone; and as nitriles, mention is more particularly made of acetonitrile. A mixture of said solvents may be used.

The extraction operation is carried out at a temperature which depends on the nature of the solvent.

This extraction step can be carried out at the same time as the acidification. However, it is preferable for the reaction mixture and the organic solvent to be mixed together, and then for the acid to be added.

In order to isolate the alkoxyhydroxybenzaldehyde (vanillin and/or ethylvanillin) from the extraction solvent, a separation step can be carried out by recrystallization, but a distillation of said mixture is preferably carried out, making it possible to obtain, for example at the top of the distillation, the extraction solvent (if it is the most volatile compound of the mixture) and, for example at the bottom of the distillation, a "crude alkoxyhydroxybenzaldehyde" ("crude" vanillin and/or ethylvanillin), namely a mixture comprising essentially the alkoxyhydroxybenzaldehyde, combined with heavy impurities called "tars" and with small amounts of light impurities. Reference is made, for this step in particular, to the process described in patent application WO 2010/007161.

The organic solvent used is advantageously recycled. It can be reintroduced into the process in order to extract the alkoxyhydroxybenzaldehyde from the aqueous phase during the acidification, and/or used to recover the alkoxyhydroxybenzaldehyde from the washing water.

Optionally, the alkoxyhydroxybenzaldehyde can be treated in order to condition it in solid form. Preferably, the alkoxyhydroxybenzaldehyde is purified, preferably by distillation, followed by crystallization (using one or more solvents or by the flaking technique), for example according to the following steps:

dissolution of the alkoxyhydroxybenzaldehyde in a water-alcohol mixture (for example methanol or ethanol);
vacuum crystallization;
batchwise pulling dry;
drying of the alkoxyhydroxybenzaldehyde at a temperature of 25° C. at a temperature below the melting point of the alkoxyhydroxybenzaldehyde, preferably under an inert gas (typically nitrogen).

Several crystallization variants can be envisioned: for example batchwise crystallization, for example by cooling, or continuous crystallization, for example under vacuum.

The resulting product can be optionally ground so as to obtain finer grains.

EXAMPLES

In the examples, the degree of conversion, the yield and the selectivity obtained are defined.

The degree of conversion (DC) corresponds to the ratio between the number of moles of reagent (hydroxyphenol, for example) converted and the number of moles of reagent (hydroxyphenol, for example) used.

The real yield (RY) is expressed by the ratio between the number of moles of product formed (alkoxyphenol, for example) and the number of moles of reagent used (hydroxyphenol, for example).

The selectivity or the yield with respect to the converted product (YC) is expressed by the ratio between the number of moles of product formed (alkoxyphenol, for example) and the number of moles of reagent converted (hydroxyphenol, for example).

Hydroxyphenol O-alkylation

Examples 1 to 4 (Hydroquinone—"HQ")

The following are charged batchwise, at 80° C., to a 150-liter 316L stainless steel reactor equipped with a jacket, with a mechanical stirrer, with a reflux condenser system and with an inert gas (nitrogen) inlet:

21.9 kg (0.20 kmol) of crystalline hydroquinone (HQ)
x kg of demineralized water (cf. table below)
2.6 kg (0.02 kmol) of an aqueous solution of sodium hydroxide at 30% by weight
y kg of methyl isobutyl ketone (MIBK) (cf. table below).

The following are simultaneously injected into the reactor containing the above aqueous solution, over the course of 45 minutes under 10 bar at a temperature of 120° C.:

28.3 kg (0.21 kmol) of an aqueous solution of sodium hydroxide at 30% by weight
11.1 kg (0.22 kmol) of methyl chloride.

After reaction for 1.5 hours, the reaction medium is cooled to 30° C. and transferred to the "neutralization" section. A sample of this reaction medium is taken in order to assay, by liquid chromatography, the compounds present (p-methoxyphenol PMP and p-dimethoxybenzene PDMB, and HQ) in the mixture and to determine the reaction performance levels.

| Examples | 1 | 2 | 3 | 4 |
|---|---|---|---|---|
| Water (x kg) | 43.8 | 30.7 | 12.1 | 0 |
| MIBK (y kg) | 12.7 | 19.1 | 28.7 | 39.0 |
| MIBK/HQ (ml/mol) | 80 | 120 | 180 | 245 |
| DC (HQ) | 85% | 87% | 89% | 89% |
| RY(PMP)/HQ | 65% | 70% | 71% | 71% |
| RY(PDMB)/HQ | 20% | 18% | 16% | 16% |
| R = dialkoxybenzene/ alkoxyphenol (w/w) | 0.34 | 0.29 | 0.25 | 0.25 |

Observation: An aqueous solution of hydroquinone can be prepared beforehand.

These examples illustrate the effect of the amount of organic solvent on the dialkoxybenzene/alkoxyphenol ratio and in particular on the p-dimethoxybenzene/p-methoxyphenol ratio. Above a certain amount of organic solvent, there is no effect of the amount of organic solvent on the dialkoxybenzene/alkoxyphenol ratio. On the other hand, below a certain amount of organic solvent, the invention illustrates the effect on the dialkoxybenzene/alkoxyphenol ratio. This is surprising for those skilled in the art who were not expecting such an effect.

Thus, it is possible to adjust the synthesis preferentially toward one or other of the compounds according to the market demands, i.e. to be able to form to a greater or lesser extent the compound of the dialkoxybenzene type compared with the alkoxyphenol, and vice versa, by using the amount of organic solvent. Thus, the invention relates to a process for producing at least one alkoxyphenol from at least one hydroxyphenol which makes it possible to modulate or adjust the production of the dialkoxybenzene/alkoxyphenol ratio. Furthermore, this effect is observed on an industrial process for which the conversion of the starting hydroxyphenol is maximized.

Hydroxyphenol O-alkylation

Examples 5 to 7 (Pyrocatechol—"PC")

The following are charged batchwise, at 80° C., to a 150-liter 316L stainless steel reactor equipped with a jacket, with a mechanical stirrer, with a reflux condenser system and with an inert gas (nitrogen) inlet:

21.2 kg (0.19 kmol) of crystalline pyrocatechol (PC)
30.7 kg of demineralized water
2.5 kg (0.019 kmol) of an aqueous solution of sodium hydroxide at 30% by weight
x kg of methyl isobutyl ketone (MIBK) (cf. table below).

The following are simultaneously injected into the reactor containing the above aqueous solution, over the course of 45 minutes under 10 bar at a temperature of 120° C.:

21.8 kg (0.164 kmol) of an aqueous solution of sodium hydroxide at 30% by weight
8.9 kg (0.176 kmol) of methyl chloride.

After reaction for 1.5 hours, the reaction medium is cooled to 30° C. and transferred to the "neutralization" section. A sample of this reaction medium is taken in order to assay, by liquid chromatography, the compounds present (guaiacol GA and veratrole VE and residual PC) in the mixture and to determine the reaction performance levels.

| Examples | 5 | 6 | 7 |
|---|---|---|---|
| MIBK (x kg) | 12.3 | 18.5 | 27.8 |
| MIBK/PC (ml/mol) | 80 | 120 | 180 |
| DC (PC) | 79% | 79% | 80% |
| RY(GA)/PC | 72.1% | 72.4% | 74.5% |
| RY(VE)/PC | 7.3% | 6.6% | 5.4% |
| R = dimethylated/ monomethylated (w/w) | 0.11 | 0.10 | 0.08 |

Observation: An aqueous solution of pyrocatechol can be prepared beforehand.

These examples illustrate the effect of the amount of organic solvent on the dialkoxybenzene/alkoxyphenol ratio and in particular on the veratrole/guaiacol ratio.

As for examples 1 to 4, above a certain amount of organic solvent, there is no effect of the amount of organic solvent on the dialkoxybenzene/alkoxyphenol ratio. On the other hand, below a certain amount of organic solvent, the invention illustrates the effect on the dialkoxybenzene/alkoxyphenol ratio. This is surprising for those skilled in the art who were not expecting such an effect.

Thus, it is possible to adjust the synthesis preferentially toward one or other of the compounds according to the market demands, i.e. to be able to form to a greater or lesser extent the compound of the dialkoxybenzene type compared with the alkoxyphenol, and vice versa, by using the amount of organic solvent. Thus, the invention relates to a process for producing at least one alkoxyphenol from at least one hydroxyphenol which makes it possible to modulate or adjust the production of the dialkoxybenzene/alkoxyphenol ratio. Furthermore, this effect is observed on an industrial process for which the conversion of the starting hydroxyphenol is maximized.

Condensation

The following are continuously charged to a first 5-liter 316L stainless steel reactor equipped with a jacket, with a mechanical stirrer, with a pH electrode, with a reflux condenser system and with an inert gas inlet:

64.8 kg/h of demineralized water
9.3 kg/h (116 mol/h) of an aqueous solution of sodium hydroxide at 50% by weight
10.1 kg/h (81.5 mol/h) of guaiacol (new and recycled from which all or part of the veratrole has been removed).

This reaction mixture is maintained at a temperature of 35° C. This preparation is then fed into the first reactor of a system of 3 reactors in cascade, with an aqueous solution of glyoxylic acid at 50% by weight (6.04 kg/h, i.e. 40.8 mol/h).

The 3 perfectly stirred reactors are made of 316L stainless steel and each have a volume of 80 l; they operate at 35° C.

The overall residence time is 2 hours.

At the outlet of the final reactor, a sample of this reaction medium is taken and the compounds present in the mixture are assayed by liquid chromatography.

The results obtained are as follows:
conversion of guaiacol (GA): DC=47%
4-hydroxy-3-methoxymandelic acid (PMA): YC(PMA)/GA=86%
2-hydroxy-3-dimethoxymandelic acid: YC(OMA)/GA=5%
2-hydroxy-3-methoxy-1,5-dimandelic acid: YC(DMA)/GA=9%

The reaction medium is sent to recycling loop 1 in order to separate the excess guaiacol from the mandelic compounds.

Oxidation

The 316L stainless steel oxidation reactor equipped with a self-suction stirrer of cavitation type ("cavitator") or of Rushton type and with a jacket for efficient cooling is continuously fed with:

the mixture of the co-catalysts and of the aqueous solution of mandelic compounds from loop 1, i.e.:
- 77 kg/h of reaction medium resulting from the condensation reaction, in which the excess guaiacol is removed (then recycled) in recycling loop 1. This mixture contains about 7.2 kg/h of 4-hydroxy-3-methoxymandelic acid, 0.5 kg/h of 2-hydroxy-3-methoxymandelic acid and 0.9 kg/h of 2-hydroxy-3-methoxy-1,5-dimandelic acid.
- 100 g/h of an aqueous solution of $CoCl_2$ and of $CuSO_4$ in an amount expressed as molar percentage of metal relative to the molar sum of the mandelic acids: 0.04% each;

the appropriate amount of an aqueous solution of sodium hydroxide at 50% by weight corresponding at least to the amount required by the stoichiometry of the oxidation reaction (to be discussed together);

the amount of oxygen at atmospheric pressure sufficient to have a virtually complete conversion of the mandelic acids. The oxidizing agent may be oxygen at atmospheric pressure or pressurized air.

This reaction is carried out at 80° C. At the outlet of the reactor, a sample of this reaction medium is taken and the compounds present in the mixture are assayed by liquid chromatography.

The results obtained are as follows:

conversion of 4-hydroxy-3-methoxymandelic acid: DC>99.5%

Yield of vanillin VA:

YC(VA)/PMA=98%

The reaction medium is sent to the loop for extraction of the sodium vanillate from the aqueous phase (termed recycling loop 2).

The invention claimed is:

1. A process for producing alkoxyphenol, the process comprising O-alkylating at least one hydroxyphenol to give at least one alkoxyphenol, wherein said O-alkylating comprises using an O-alkylating agent, an aqueous solvent comprising a Broensted base, and an organic solvent, with a base/O-alkylating agent ratio of between 0.5 and 1.5 in moles of base per mole of O-alkylating agent, an O-alkylating agent/hydroxyphenol ratio of between 0.5 and 2 mol of O-alkylating agent per mole of hydroxyphenol, and an organic solvent/hydroxyphenol ratio of less than 150 ml of organic solvent per mole of hydroxyphenol.

2. A process for producing alkoxyhydroxybenzaldehyde, the process comprising O-alkylating at least one hydroxyphenol to give at least one alkoxyphenol as claimed in claim 1, and introducing an aldehyde function on the alkoxyphenol so as to obtain the corresponding alkoxyhydroxybenzaldehyde.

3. The process as claimed in claim 2, wherein the hydroxyphenol is pyrocatechol, wherein the O-alkylating is O-methylation and/or O-ethylation, wherein the alkoxyphenol is selected from guaiacol and/or guaethol, and wherein the alkoxyhydroxybenzaldehyde is selected from vanillin and/or ethylvanillin.

4. The process as claimed in claim 2, wherein the process comprises at least the following steps:
- condensing the alkoxyphenol compound with glyoxylic acid so as to obtain the corresponding mandelic compound;
- separating the alkoxyphenol compound from the mandelic compound, and optionally recycling the alkoxyphenol compound;
- oxidizing the mandelic compound so as to obtain the alkoxyhydroxybenzaldehyde;
- separating the alkoxyhydroxybenzaldehyde by extraction with an organic solvent, then separating the alkoxyhydroxybenzaldehyde from the organic solvent, and optionally recycling the organic solvent; and
- recovering the alkoxyhydroxybenzaldehyde, optionally in solid form.

5. The process as claimed in claim 4, wherein separating the alkoxyphenol compound from the mandelic compound comprises the following steps:
- recovering a mixture comprising the mandelic compound formed in mandelate form and the unreacted alkoxyphenol in alkoxyphenolate form;
- neutralizing the alkoxyphenolate to give the alkoxyphenol, while maintaining the corresponding mandelate in salified form;
- separating the alkoxyphenol from the mandelate;
- introducing the mandelate into an oxidation reactor; and
- recycling the alkoxyphenol, which has not reacted as a reagent, to the condensation reaction.

6. The process as claimed in claim 2, wherein the process comprises:
- separating the alkoxyhydroxybenzaldehyde from the reaction mixture by extraction with an organic solvent; and
- recovering and recycling the organic solvent used for the extraction.

7. The process as claimed in claim 1, wherein obtaining the alkoxyphenol comprises the following steps:
- O-alkylating at least one hydroxyphenol to give alkoxyphenol in a basic multiphase medium comprising an organic phase and an aqueous phase;
- acidifying the resulting reaction medium;
- separating the organic phase containing the alkoxyphenol compound from the aqueous phase containing the Broensted base and recovering the alkoxyphenol compound.

8. The process as claimed in claim 1, wherein the process consists of producing guaiacol and/or of guaethol from pyrocatechol or producing para-methoxyphenol and/or para-ethoxyphenol from hydroquinone, by O-methylation and/or O-ethylation of one of the hydroxyl groups of the pyrocatechol or hydroquinone.

9. The process as claimed in claim 1, wherein the O alkylating is carried out in a basic multiphase medium with an organic solvent/water ratio, of less than 1.5 by weight.

10. A process for producing at least one alkoxyhydroxybenzaldehyde compound, said process comprising:
- (i)—synthesizing at least one alkoxyphenol from at least one hydroxyphenol in the presence of at least one O-alkylating agent as claimed in claim 1;
- (ii)—recovering at least one alkoxyphenol and impurities, including a dialkylated compound of the dialkoxybenzene type;
- (iii)—separating the dialkoxybenzene from the alkoxyphenol;
- (iv)—condensing the alkoxyphenol with glyoxylic acid and obtaining the corresponding mandelic compound;
- (v)—oxidizing the mandelic compound to give the corresponding alkoxyhydroxybenzaldehyde; and
- (vi)—recovering the alkoxyhydroxybenzaldehyde optionally in solid form.

11. The process as claimed in claim 10, wherein the at least one alkoxyhydroxybenzaldehyde is selected from vanillin (4-hydroxy-3-methoxybenzaldehyde) and ethylvanillin (3-ethoxy-4-hydroxybenzaldehyde) and wherein the hydroxyphenol is pyrocatechol.

12. The process as claimed in claim 1, wherein the organic solvent/hydroxyphenol ratio is between 10 and 150 ml of organic solvent per mole of hydroxyphenol.

13. The process as claimed in claim 2, wherein introducing the aldehyde function occurs via a condensation reaction between the alkoxyphenol and glyoxylic acid followed by oxidation of the compound formed.

14. The process as claimed in claim 3, wherein introducing the aldehyde function occurs via a condensation reaction between the alkoxyphenol and glyoxylic acid followed by oxidation of the compound formed.

15. The process as claimed in claim 9, wherein the basic multiphase medium has an organic solvent/water ratio of less than 1.2 by weight.

\* \* \* \* \*